United States Patent
Davis

(12) United States Patent    (10) Patent No.: US 7,602,884 B1
Davis    (45) Date of Patent: Oct. 13, 2009

(54) CONCRETE RADIOGRAPHY

(75) Inventor: James Davis, Fallbrook, CA (US)

(73) Assignee: Davis Laboratories, Inc., Brea, CA (US)

( * ) Notice: Subject to any disclaimer, the term of this patent is extended or adjusted under 35 U.S.C. 154(b) by 0 days.

(21) Appl. No.: 12/136,245

(22) Filed: Jun. 10, 2008

(51) Int. Cl.
    *H05G 1/28* (2006.01)
    *G01N 23/04* (2006.01)

(52) U.S. Cl. .................................. 378/163; 378/62

(58) Field of Classification Search .............. 378/4, 378/19, 70, 62, 162, 163, 207
See application file for complete search history.

(56) References Cited

U.S. PATENT DOCUMENTS

| | | | | |
|---|---|---|---|---|
| 5,052,035 A | * | 9/1991 | Krupnick | 378/163 |
| 5,299,254 A | * | 3/1994 | Dancer et al. | 378/163 |
| 5,394,457 A | * | 2/1995 | Leibinger et al. | 378/162 |
| 5,469,847 A | * | 11/1995 | Zinreich et al. | 600/414 |
| 5,933,473 A | * | 8/1999 | Kitaguchi et al. | 378/57 |
| 6,118,848 A | * | 9/2000 | Reiffel | 378/65 |

* cited by examiner

*Primary Examiner*—Ed Glick
*Assistant Examiner*—Irakli Kiknadze
(74) *Attorney, Agent, or Firm*—James A. Italia; Italia IP

(57) ABSTRACT

An improved way of using radiographic imagery to locate inclusions within concrete. Radiographic film is placed on one side of a concrete structure and X-rays are transmitted towards the film from the other side. A target which is selectively radiographically impervious is interposed to generate location indicia on the film. Once developed, the film may be used to generate an image display such as a paper bearing indicia from the film or may be used directly to mark the location of inclusions on the concrete. The target may comprise a metallic plate with a viewing window and location indicia rendered in radiographically impervious material to establish measurement indicia in the final film image.

16 Claims, 5 Drawing Sheets

CONCRETE RADIOGRAPHY

FIELD OF THE INVENTION

The present invention relates to a method of viewing into the interior of concrete structures, such as columns, and more particularly, relates to method and apparatus for using radiography to generate images of the interior of concrete structures.

BACKGROUND OF THE INVENTION

It is occasionally necessary to determine location of inclusions within concrete structures, such as locating inclusions within a concrete column or slab. This situation may arise for example when contemplating core drilling or cutting through the concrete structure. It is highly desirable to avoid impinging upon inclusions, such as reinforcement bars (hereinafter referred to as rebar), conduits, post tensioning cables, and the like. It may also be desirable to discriminate among inclusions, where several inclusions are in relatively close proximity to one another.

Purposes exist other than avoiding disruption to necessary building elements. For example, it may be desirable to produce evidence for litigation purposes even if no boring or cutting is to be performed.

There exists a need in the art for determining precisely locations of inclusions embedded within concrete.

SUMMARY OF THE INVENTION

The present invention uses radiography to locate inclusions and other anomalies within concrete. According to another aspect of the invention, a target for imposing location indicia on the final radiographic image may be employed. The target may comprise a metallic plate provided with radiographically impervious material forming indicia for determining distances and enabling other indexing or referencing to locate an inclusion identified within the concrete structure being radiographed. The target may have a window formed therein, for viewing the concrete substrate against which the target is placed, for assuring correctly reproduced location of the target.

Location indicia may comprise for example concentric circles around a central reference point of the target, and measurement or zone identifiers, such as numbers, letters, and the like.

According to further aspects of the invention, the invention may comprise a method including the step of using radiography to locate inclusions within concrete.

The method may include the step of reproducing location of an inclusion on the surface of the concrete, using imagery generated directly or by additional reproductions from the developed radiographic film. The latter step is highly useful for example in preparation of core drilling the concrete, with an eye to avoiding the inclusion, or alternatively, to drilling into the inclusion. Illustratively, it is usually desirable to avoid disrupting structural elements such as rebar, post tensioning cables, and conduits. It may be desirable, however, to expose a void or a zone of concrete suspected to be defective, for example to support litigation should defective material result in litigation.

The method may include a step of providing a portable film development facility and using that facility onsite to produce immediately usable radiographic results.

It is an object of the invention, therefore, to use radiography to investigate inclusions within concrete structures.

It is another object of the invention to endow radiographic images with indicia which will assist in locating identified inclusions.

It is a further object of the invention to expedite the process of locating inclusions in concrete structures, and identifying their location externally on the concrete structure, for example, in preparation for core drilling.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
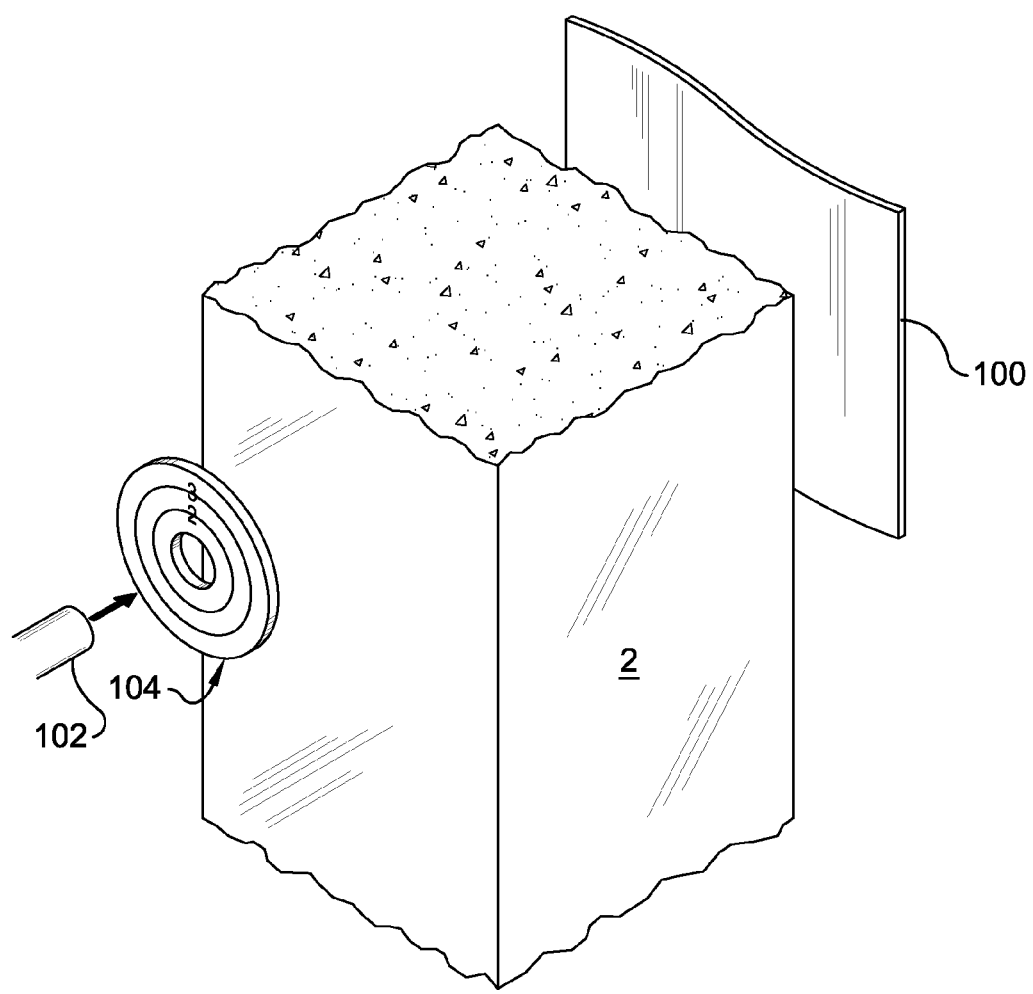
FIG. 1 is an exploded environmental perspective view of a concrete column to be radiographically imaged according to at least one aspect of the invention.

FIG. 1 shows a concrete column 2 about to be imaged using radiography, which relies on radiated energy such as X-rays to generate images on a film, such as a radiographic film 100, which has been placed behind a concrete structure such as the concrete column 2. Radiography may be conducted using only a source 102 of radiographic energy, which may be for example any known projector of X-rays, and the radiographic film 100. The source 102 may utilize radioactive cobalt or radioactive iridium (neither shown). This will produce images wherein inclusions (not shown) appear in the final image. In some types of investigation of concrete, this is sufficient to produce information being sought as to the nature of the inclusion. An inclusion may be a structural element, such as rebar, post tensioning cables, and internal conduits, embedded energy cables such as electric wires and optic fibers, anchoring elements such as anchor bolts and threaded sockets embedded within the concrete, and others. The singular and plural forms of the term inclusion will be understood to be interchangeable as used herein.

Alternatively, an inclusion may be a void or a zone where constituency of the concrete differs from elsewhere in the concrete structure 2, or is suspected of deviating from desired characteristics. Constituency may encompass chemical or other contamination, undesired ratios of cement, sand, gravel, or other usual components of concrete, unidentified objects or substances or both, or a zone wherein concrete has or may be thought to be insufficiently cured, insufficiently hydrated, or otherwise may be suspected of deviating from a desired constituency.

If the radiographic process is as described above, then radiographic energy, such as X-rays, is discharged through the concrete structure 2 and against the radiographic film 100. The radiographic film 100 may then be developed.

In a further aspect of the invention, a target 104 may be placed against the concrete column 2. It would be possible to place the target 104 between the concrete 2 and the radiographic film 100 if desired.

FIG. 1 also shows in diagrammatic or symbolic form a portable radiographic film developing facility 150 which may be brought to the site of the concrete column 2, and which may be utilized as described hereinafter.

For the purposes of this invention, a target such as the target 104 is a device for forming guidance indicia on a radiographic image (an exemplary radiographic image is presented hereinafter) of an inclusion contained within a substrate. The guidance indicia are formed simultaneously with exposing radiographic film to form the radiographic image. Thus the inclusion or anomalies and the guidance indicia are formed in one film exposure operation on the same image.

A target such as the target 104 may comprise a plate of radiographically pervious material bearing radiographically impervious masking material for forming the guidance indicia on the final radiographic image.

Figure 2:
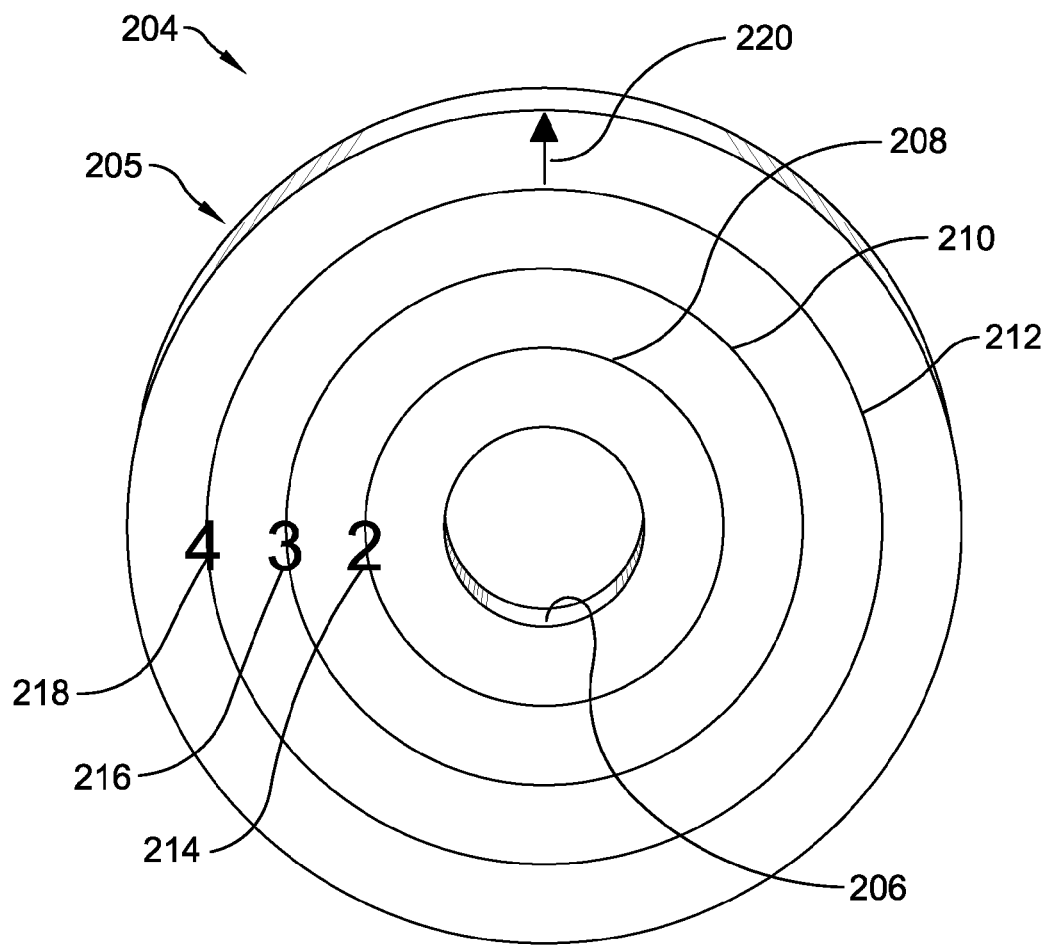
FIG. 2 is a plan view of a target which may be employed with radiographic imaging of concrete according to at least one aspect of the invention, and is drawn to enlarged scale.

FIG. 2 shows an exemplary target 204. The target 204 may comprise a disc or circular plate 205 of aluminum having a central circular opening or window 206. A plurality of concentric, spaced apart lead filled grooves 208, 210, 212 may be introduced into the plate 205 so as to concentrically surround the window 206. The lead filled grooves 208, 210, and 212 serve as radiographically impervious perimetric visual boundary elements which concentrically surround the window so as to cause corresponding perimetric indicia surrounding the window to appear on the final radiological image. A target such as the target 204 may have no perimetric visual boundary elements, one perimetric visual boundary elements, or a plurality of perimetric visual boundary elements.

Numerical indicia 214, 216, 218 uniquely identify each one of the grooves 208, 210, 212. Additional indicia, such as an arrow 220, may be provided, for example to indicate a desired vertical direction when mounting the target 204 on a concrete structure, such as the concrete column 2. All of the indicia 208 . . . 220 described thus far may be rendered in a radiographically impervious material such as lead, so that corresponding elements appear in a radiographic film, such as the radiographic film 100 after development of the film. Advantageously, each perimetric visual boundary element has associated therewith respective unique indicia rendered in the masking material. As a consequence, corresponding perimetric indicia which are identifiable by one of the unique indicia will be generated in the final radiographic image.

Because of the circular grooves 208, 210, and 212, the target 204 enables inclusions which appear in the image of developed film to be located at any radial direction from the central opening 206.

A target such as the target 104 or the target 204 may be fabricated from a metal which is essentially radiographically pervious, such as aluminum, with the masking material being fabricated from another metal such as lead which is essentially radiographically impervious. Of course, the target need not be limited to these constructions. Other radiographically pervious and impervious materials may be substituted for aluminum and lead respectively. Illustratively, a target could be fabricated from papers and polymeric materials such as Mylar. Where employed herein, aluminum will be understood to include both pure aluminum and also its alloys. Similarly, lead will be understood to include both pure lead and also its alloys. Designation of a specific metal such as lead or aluminum connotes substantial constituency of the named metal, such as greater than fifty percent by weight.

It should be made clear that the grooves 208, 210, and 212 need not be complete circles. It is merely desirable that the actual grooves form enough of a circle to create the visual impression of a circle. For example, instead of a full circular line as depicted, each groove, such as the grooves 208, 210, and 212 may comprise a series of unconnected line segments (not shown), provided that the overall dominant impression is that of a circular line. The grooves 208, 210, and 212, in addition to indicia elements 214 . . . 220 are filled with lead or another radiographically impervious material, so that they generate corresponding visual elements in the developed film after radiography is complete. Grooves such as the grooves 208, 210, and 212 which are rendered in a radiographically impervious material will hereinafter be referred to as a perimetric visual boundary element.

Figure 3:
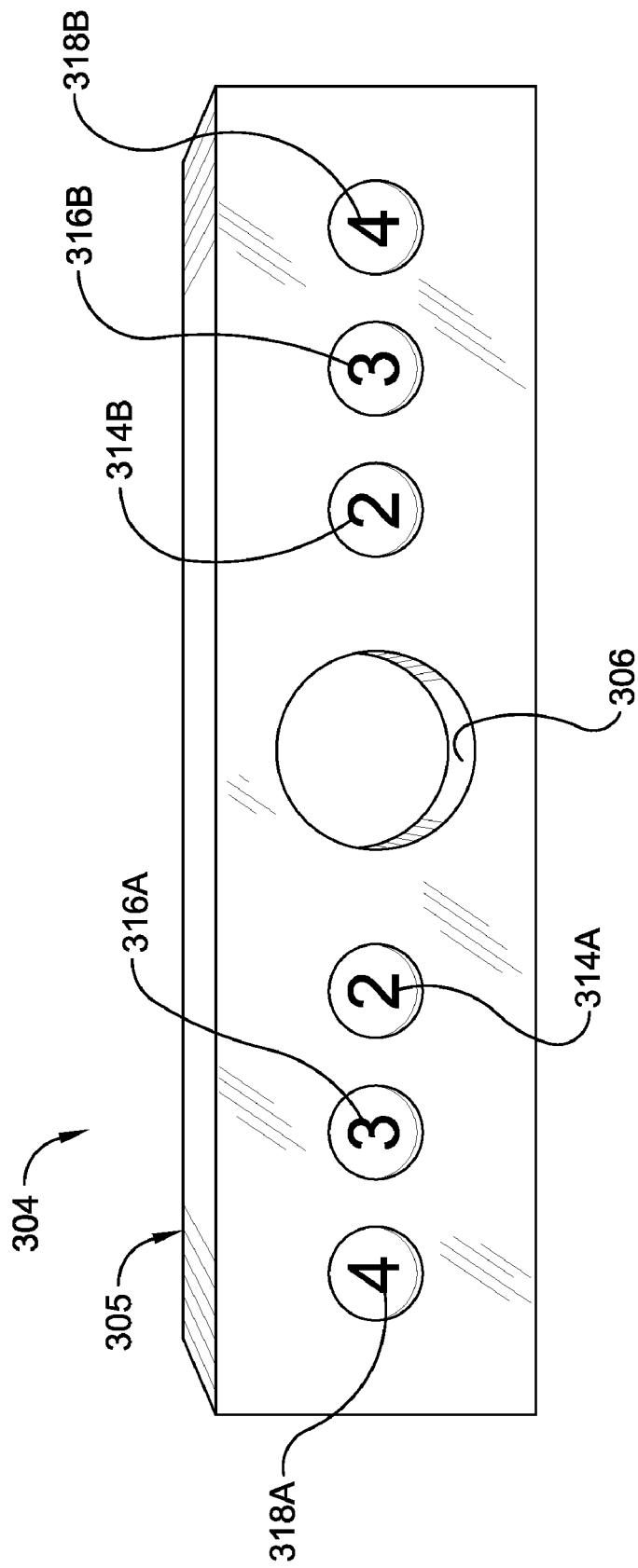
FIG. 3 is a plan view of another target may be employed with radiographic imaging of concrete according to at least one aspect of the invention, and is drawn to enlarged scale.

FIG. 3 shows a target 304 according to a further aspect of the invention. The target 304 may comprise a rectangular plate 305 in which may be formed a circular opening or window 306, and numerical indicia for indicating proximity to the central reference point which may be established by the window 306. The indicia 314A, 314B, 316A, 316B, 318A, and 318B may be formed for example by filling circular grooves (not separately shown) with a radiographically impervious material such as lead, then routing out the lead to form individual characters. Using this method, the final image of the developed film will generate an image wherein each numeral will appear as a light numeral against a dark background. It would be possible, of course, to machine a numeral or other character (none shown) into the target 304 and fill the machined numeral with lead or other radiographically impervious material.

The indicia 314A, 314B, 316A, 316B, 318A, and 318B may serve as markings which are spaced at regular intervals and which are arrayed colinearly with the center of the central opening 206. This arrangement may be employed for example where a point located along a linear construction element such as a rebar is of interest, and where it is not necessary to locate the point of interest at different radii from a known point within the concrete.

The central opening, such as the central opening 206 of FIG. 2 may be regarded as a means for enabling an observer to ascertain the precise location of the target on the substrate by direct viewing of the substrate when the target is placed thereagainst. Utility of the central opening is not restricted merely to direct viewing. It may also serve as a guide for spray painting or other marking, application of adhesives, an access port for driving fasteners into the concrete, or any other purpose in furtherance of investigation of inclusions, remediation thereof, and subsequent construction operations.

Means for enabling an observer to ascertain the precise location of the target on the substrate may also be regarded as providing apparatus for fixing the target in place on the concrete stratum, such as arms arranged to clamp the target to a concrete structure such as the column 2. In place of arms, bands, wire ties, bungee cords, and other devices may be utilized to similar effect.

The central opening such as the central opening 206 of FIG. 2 or the central opening 306 of FIG. 3 may establish a central reference point, which may be for example the center of the central opening. Markings such as the numerical indicia 214, 216, and 218 of FIG. 2 or 314, 316, and 318 of FIG. 3, may be spaced at regular intervals radiating from the central reference point to enable estimation or even direct measurement of inclusions from this reference point. The central reference point may be conveniently centered within the central opening or otherwise contained within the central opening.

The various indicia including a radiographically impervious portion, such as the indicia or markings 208, 210, 212, 214, 216, 218, 220, 314A, 314B, 316A, 316B, 318A, and 318B, form indicia in the final developed image which collectively establish an index against which location of an inclusion within the concrete structure can be referenced.

The central opening such as the central opening 206 may serve as means for enabling an observer to ascertain the precise location of the target on the substrate, and as depicted in FIG. 2, comprises a circular window formed in and extending entirely through the plate 205. Additional means for enabling an observer to ascertain the precise location of the target on the substrate include utilizing a symmetrical or non-symmetrical target and tracing about the perimeter with chalk, pencil or other similar material on the substrate, applying a transferable material to the side of the target that comes in contact with the substrate and thereby leaving "fingerprint" of the location of the target on the substrate, and utilizing a representative of the target (such as a paper version) to act as a place holder once the target is removed, and any other similar means.

Figure 4:
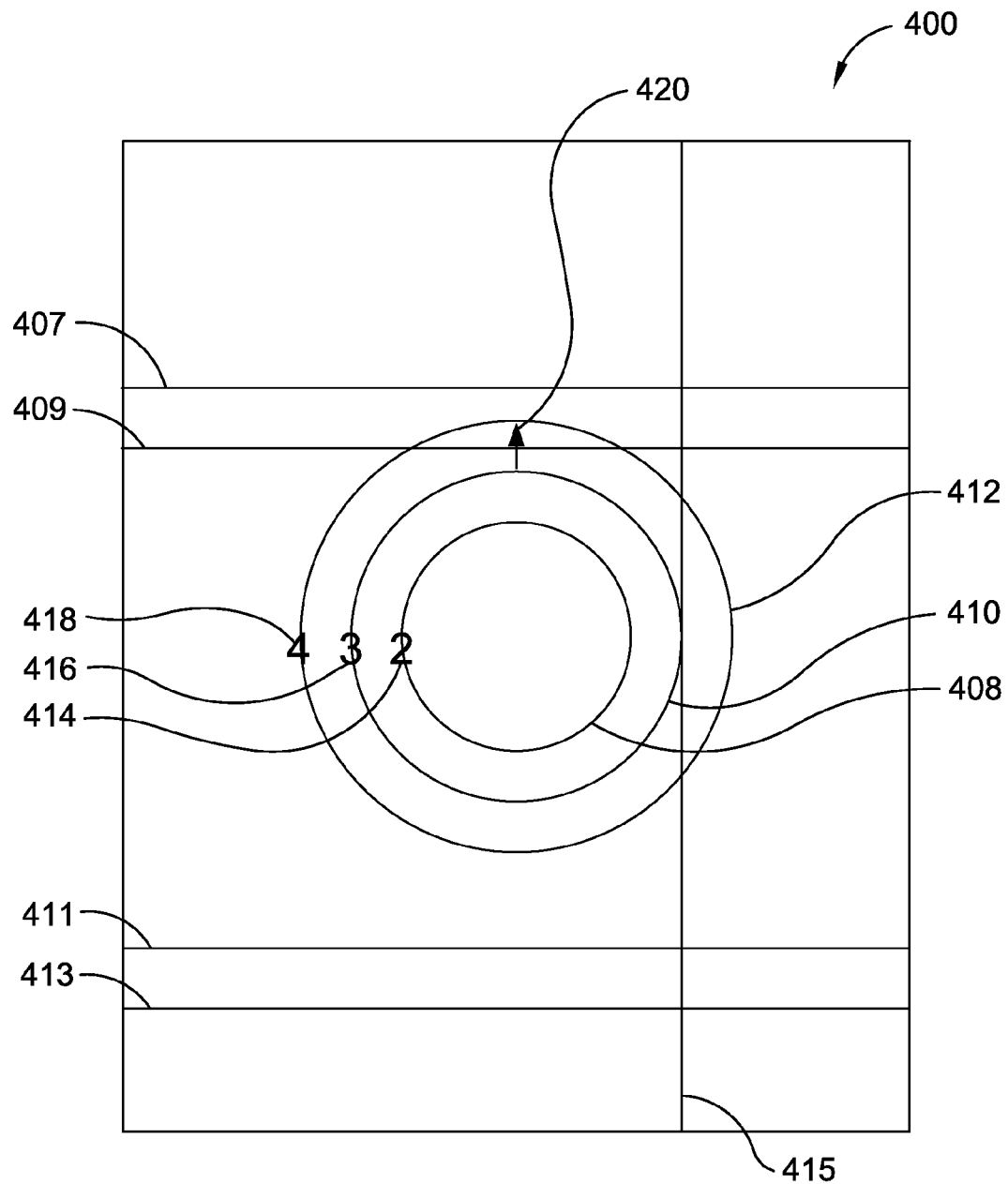
FIG. 4 represents a radiographic image which may be captured using apparatus or method or both, according to at least one aspect of the invention.

FIG. 4 shows an illustrative image 400 which may result from exposing and developing for example a radiographic film 403, using the target 204 of FIG. 2. The image 400 may have darkened lines 407, 409, 411, 413, and 415, which indicate rebar embedded the concrete structure which has been imaged. The image 400 may have elements appearing as circular lines 408, 410, and 412, numerals 414, 416, and 418, and an arrow 420. The visual elements 408 . . . 420 all reflect the masking material which has defined corresponding shapes in the target 204. The final radiographic image 400 therefore reveals visual elements 407 . . . 415 which correspond to construction elements contained within the concrete structure and also indexing marks 412 . . . 420, all in one image.

The image 400 will appear on a stratum such as the film 100 after development after the radiographic image is captured, or alternatively on any stratum such as paper, polymeric sheet, or any other desired material, using any reproductive technique to transfer the image, such as the image 400 from the developed film to another selected material. Reproductive techniques may be of the analog type, such as xerography, or may be indirect, such as by digitizing the image prior to imposing the image onto a selected stratum. Digitized data may be transmitted remotely if desired in any known way, such as by radio frequency signals, optical signals, by using the internet, or by using any communications channel incorporating diverse data transmission methods. Remote transmission enables a remote observer to perform analysis or consider the image for any purpose expeditiously.

Figure 5:
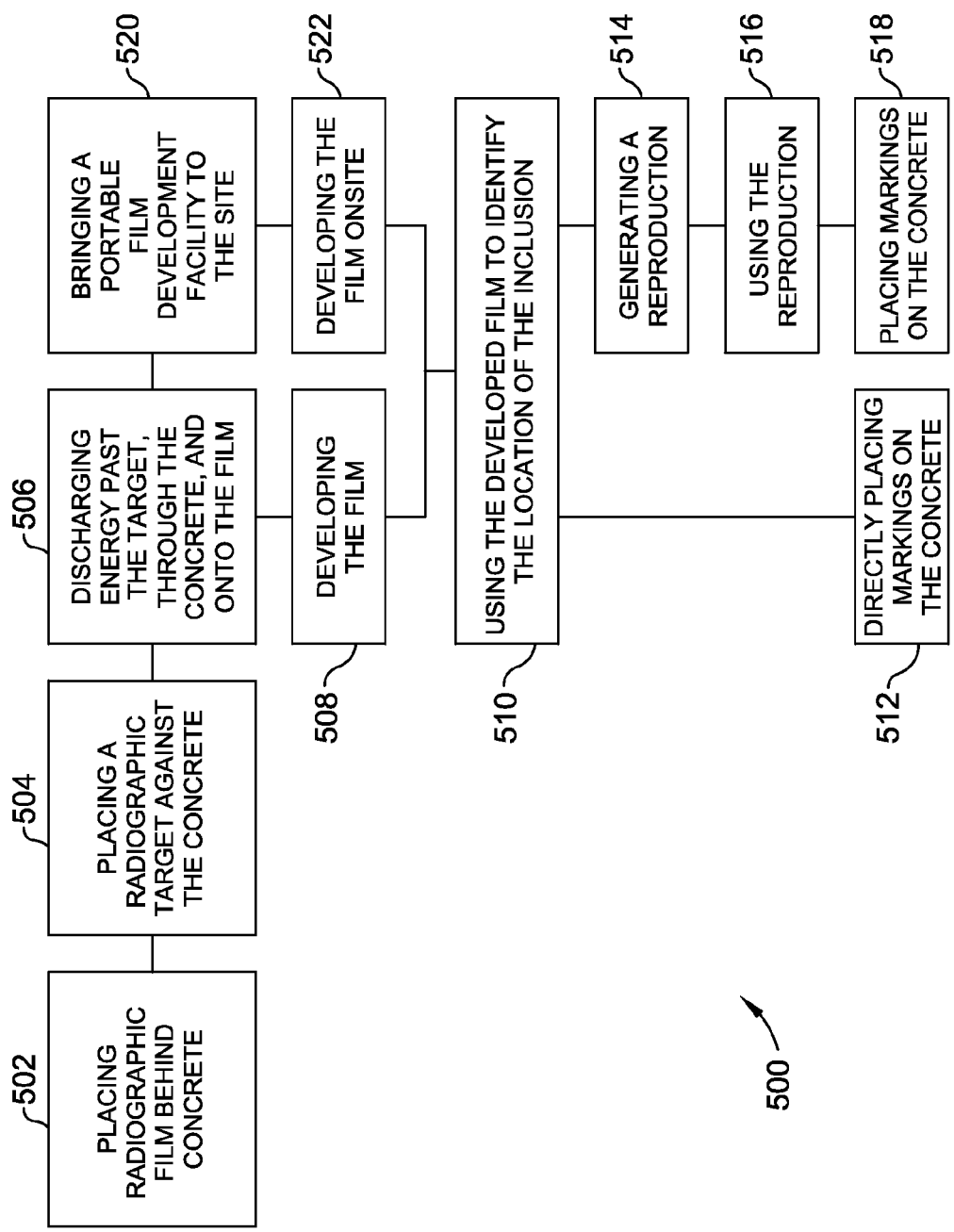
FIG. 5 is a block diagram summarizing steps of a method according to at least one aspect of the invention, and is read starting at the upper left.

According to at least one further aspect, and as summarized in FIG. 5, the invention may comprise a method 500 of generating one or more images, such as the image 400, of internal characteristics of a concrete structure, such as the concrete structure 2. The method may comprise:

a step 502 of placing radiographic film, such as the radiographic film 100, behind the concrete structure; a a step 504 of placing against the concrete structure a radiographic target, such as the target 204, having a radiographically pervious portion and a radiographically impervious portion, the latter forming indicia establishing an index against which location of an inclusion within the concrete structure can be referenced;

a step 506 of discharging radiographic energy past the radiographic target, through the concrete structure, and against the radiographic film;

a step 508 of developing the radiographic film; and a step 510 of using the developed film to identify the location of the inclusion with respect to the surface of the concrete.

From this point, the path of steps of the method 500 may diverge since the image captured on the developed film, such as the image 400, may be utilized directly or indirectly. In utilizing the image directly, the method 500 may comprise a step 512 of placing markings directly on the concrete using the developed film as a guide. Subsequent operations such as drilling a core may then proceed, with the location of the inclusion now marked on the concrete being drilled.

According to another aspect of the invention wherein the image is utilized indirectly, the step 510 of using the developed film may comprise the further step 514 of generating a reproduction from the developed film. The reproduction may comprise paper prints, polymeric strata bearing the image, slides or other basis for optical projection of the image, or still other forms of reproduction (specific reproductions are not shown).

A step 516 of using the reproduction to identify the location of the inclusion within the concrete may then be performed.

The step 516 may be followed by a step 518 of placing markings on the concrete using the reproduction.

With the location of the inclusion marked, core drilling or other operations may then be performed.

Of course, it would be possible to introduce markings for example by tracing over an optical image, where an optical method is used.

The method 500 may comprise a further step 520 of bringing a portable radiographic film development facility to the site of the concrete, and another step 522 of developing the radiographic film onsite using the portable radiographic film development facility. The steps 520 and 522 are an alternative to the step 508. The steps 510, 512, 514, 516, and 518 may be practiced using either the step 508 or alternatively, the steps 520 and 522.

The target may be placed other than on that side of the concrete structure being radiographed which is opposite to the radiographic film. For example, a film holder (not shown) may be modified to include elements which hold the target in place. In such a case, the target would be located between the concrete structure and the radiographic film. Alternatively, the target may be secured between the concrete structure and the radiographic film using retention elements which are not integrated into a film holder.

I claim:

1. A target for forming guidance indicia on a radiographic image of an inclusion contained within a concrete substrate, simultaneously with exposing radiographic film to form the radiographic image, comprising:

a plate of radiographically pervious material bearing radiographically impervious masking material for forming the guidance indicia on the final radiographic image; and means for enabling an observer to ascertain the precise location of the target within the concrete substrate.

2. The target according to claim 1, wherein the plate is fabricated from a metal which is essentially radiographically pervious and the masking material is fabricated from another metal which is essentially radiographically impervious.

3. The target according to claim 2, wherein the plate is fabricated from a material which is substantially aluminum in composition and the masking material is substantially lead in composition.

4. The target according to claim 1, wherein the target has a central reference point and the indicia includes markings spaced at regular intervals radiating from the central reference point.

5. The target according to claim 4, wherein the central reference point is contained within the means for enabling an observer to ascertain the precise location of the target on the concrete substrate.

6. The target according to claim 4, wherein the markings spaced at regular intervals are arrayed colinearly with the center of the means for enabling an observer to ascertain the precise location of the target on the concrete substrate.

7. The target according to claim 1, wherein the means for enabling an observer to ascertain the precise location of the target on the concrete substrate comprises a circular window formed in and extending entirely through the plate.

8. The target according to claim 1, wherein the means for enabling an observer to ascertain the precise location of the target on the concrete substrate comprises a window formed in and extending entirely through the plate, and wherein the plate has formed therein at least one radiographically impervious perimetric visual boundary element which concentrically surrounds the window so as to cause corresponding perimetric indicia surrounding the window to appear on the final radiological image.

9. The target according to claim 8, wherein the plate has a plurality of perimetric visual boundary elements which concentrically surround the window so as to cause corresponding concentric perimetric indicia to appear on the final radiographic image.

10. The target according to claim 9, wherein each one of the plurality of perimetric visual boundary elements is visually circular, and each one of the perimetric visual boundary elements has associated therewith respective unique indicia rendered in the masking material, whereby each one of the perimetric visual boundary elements generates corresponding perimetric indicia in the final radiographic image which is identifiable by one of the unique indicia in the final radiographic image.

11. A method of generating images of internal characteristics of a concrete structure, comprising the steps of:
   placing radiographic film behind the concrete structure;
   placing against the concrete structure a radiographic target having a radiographically pervious portion and a radiographically impervious portion, the latter forming indicia establishing an index against which location of an inclusion within the concrete structure is referenced; and
   discharging radiographic energy past the radiographic target, through the concrete structure, and onto the radiographic film.

12. The method according to claim 11, comprising the further steps of:
   developing the radiographic film; and
   using the developed film to identify the location of the inclusion with respect to the surface of the concrete.

13. The method according to claim 12, wherein the step of using the developed film comprises the further step of placing markings directly on the concrete using the developed film as a guide.

14. The method according to claim 11, comprising the further steps of:
   developing the radiographic film;
   generating a reproduction of the image contained on the developed film; and
   using the reproduction to identify the location of the inclusion with respect to the surface of the concrete.

15. The method according to claim 14, wherein the step of using the reproduction comprises the further step of placing markings directly on the concrete using the reproduction as a guide.

16. The method according to claim 11, comprising the further steps of:
   bringing a portable radiographic film development facility to the site of the concrete; and
   developing the radiographic film onsite using the portable radiographic film development facility.

* * * * *